US012599734B2

(12) United States Patent
Tang

(10) Patent No.: US 12,599,734 B2
(45) Date of Patent: Apr. 14, 2026

(54) SYSTEM AND METHOD FOR POINT-OF-DELIVERY PATIENT OXYGEN SUPPLY MONITORING

(71) Applicant: Baltimore Respiratory Innovations Inc., Wilmington, DE (US)

(72) Inventor: Wilson Tang, Gilroy, CA (US)

(73) Assignee: Baltimore Respiratory Innovations Inc., Wilmington, DE (US)

( * ) Notice: Subject to any disclaimer, the term of this patent is extended or adjusted under 35 U.S.C. 154(b) by 0 days.

(21) Appl. No.: 18/810,069

(22) Filed: Aug. 20, 2024

(65) Prior Publication Data

US 2024/0408336 A1 Dec. 12, 2024

Related U.S. Application Data

(63) Continuation of application No. PCT/US2023/062057, filed on Feb. 6, 2023.

(Continued)

(51) Int. Cl.
*A61M 16/00* (2006.01)
*A61M 16/04* (2006.01)
(Continued)

(52) U.S. Cl.
CPC ...... *A61M 16/026* (2017.08); *A61M 16/0003* (2014.02); *A61M 16/0051* (2013.01);
(Continued)

(58) Field of Classification Search
CPC .............. A61M 16/026; A61M 16/003; A61M 16/0672; A61M 16/0875; A61M 39/10;
(Continued)

(56) References Cited

U.S. PATENT DOCUMENTS 8,545,416 B1 * 10/2013 Kayyali ............ A61M 16/0051
128/204.26
10,561,863 B1 * 2/2020 Dashevsky .......... A61B 5/6803
(Continued)

FOREIGN PATENT DOCUMENTS

WO WO-2023164365 A1 8/2023

OTHER PUBLICATIONS

International Preliminary Report on Patentability for PCT Application No. PCT/US2023/062057 mailed Sep. 6, 2024, 8 pages.
(Continued)

*Primary Examiner* — Margaret M Luarca
(74) *Attorney, Agent, or Firm* — COOLEY LLP

(57) ABSTRACT

An apparatus for patient oxygen supply monitoring includes a housing, a microcontroller, at least one sensor, and a power supply. The housing has at least one port for mechanically coupling to a gas supply tube of an oxygen gas delivery system. The microcontroller is positioned within the housing, and the at least one sensor is operably coupled to the microcontroller and positioned within the housing. The power supply is positioned within the housing and configured to supply power, during operation, to the microcontroller and to the at least one sensor. The microcontroller monitors the oxygen gas delivery system by receiving data generated by the at least one sensor when the at least one port is mechanically coupled to the gas supply tube and when oxygen is flowing through the at least one port.

15 Claims, 8 Drawing Sheets

Related U.S. Application Data

(60) Provisional application No. 63/312,490, filed on Feb. 22, 2022.

(51) Int. Cl.
    *A61M 16/06*          (2006.01)
    *A61M 16/08*          (2006.01)
    *A61M 39/10*          (2006.01)

(52) U.S. Cl.
    CPC ........ *A61M 16/04* (2013.01); *A61M 16/0672* (2014.02); *A61M 16/0875* (2013.01); *A61M 39/10* (2013.01); *A61M 2016/0027* (2013.01); *A61M 2016/0039* (2013.01); *A61M 2202/0007* (2013.01); *A61M 2202/0208* (2013.01); *A61M 2205/18* (2013.01); *A61M 2205/3327* (2013.01); *A61M 2205/3331* (2013.01); *A61M 2205/3576* (2013.01); *A61M 2205/50* (2013.01); *A61M 2205/8206* (2013.01); *A61M 2230/04* (2013.01); *A61M 2230/20* (2013.01); *A61M 2230/42* (2013.01)

(58) Field of Classification Search
    CPC ............ A61M 16/0024; A61M 16/085; A61M 16/0858; A61B 5/087; A61B 5/097
    See application file for complete search history.

(56) References Cited

U.S. PATENT DOCUMENTS

| | | | | |
|---|---|---|---|---|
| 2006/0042638 A1* | 3/2006 | Niklewski | ......... | A61M 16/0858 |
| | | | | 128/207.18 |
| 2007/0193581 A1* | 8/2007 | Laurila | ................. | A61M 16/08 |
| | | | | 128/204.23 |
| 2008/0142019 A1 | 6/2008 | Lewis et al. | | |
| 2009/0020120 A1* | 1/2009 | Schatzl | ................ | A61B 5/4839 |
| | | | | 128/204.22 |
| 2015/0021909 A1* | 1/2015 | Gulliver | .............. | A61M 16/085 |
| | | | | 285/319 |
| 2015/0059764 A1 | 3/2015 | Metelits | | |
| 2018/0028769 A1 | 2/2018 | Obenchain | | |

OTHER PUBLICATIONS

International Search Report and Written Opinion of the International Searching Authority for International Application No. PCT/US2023/062057, dated Jun. 27, 2023, 9 pages.

Invacare, "Piccolo O2 App: Quick Start Guide for iOS and Android," Quick Start Brochure, 2019, 23 pages.

Patient MPOWER, "Patient Mpower Info," retrieved from URL:https://info.patientmpower.com/ retrieved on Sep. 23, 2024, 7 pages.

Spirit Health, "Technology," retrieved from URL:https://www.spirehealth.com/technology, retrieved Sep. 23, 2024, 6 pages.

* cited by examiner

100B

Derivative/Splitter Setup

Nasal Cannula 140

111

130

120

115C
Other Technology Hub
Components (wireless
communication, processor,
memory, etc.)

115E
Optional tubing
for connection

115B
Inspiration
Sensor

115

115F
T-Connector or
splitter to allow
auxiliary flow to
reach sensors
while allowing main
flow to reach
device 115A
Flow Sensor to
Detect Oxygen
Usage

500

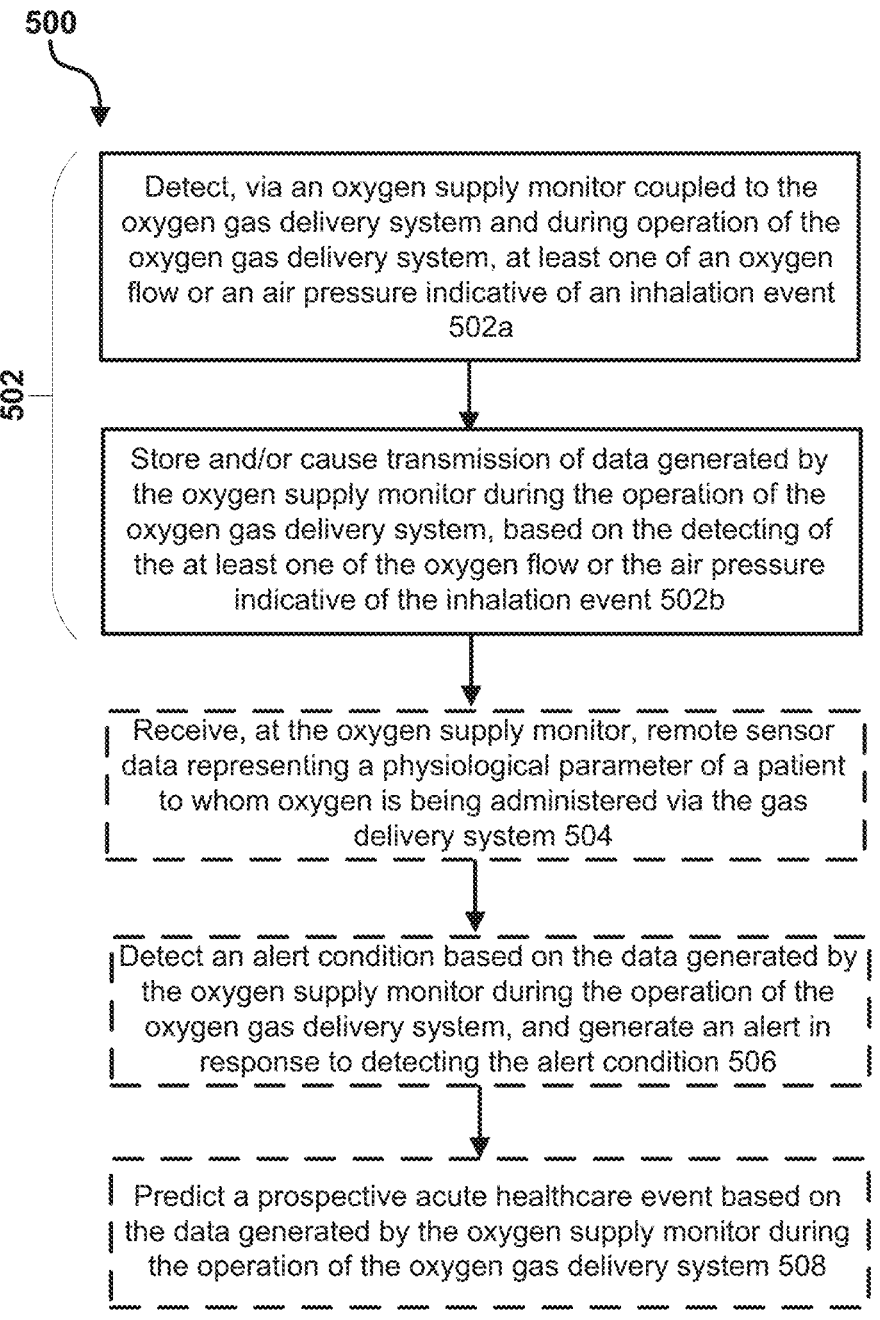

Detect, via an oxygen supply monitor coupled to the oxygen gas delivery system and during operation of the oxygen gas delivery system, at least one of an oxygen flow or an air pressure indicative of an inhalation event 502a Store and/or cause transmission of data generated by the oxygen supply monitor during the operation of the oxygen gas delivery system, based on the detecting of the at least one of the oxygen flow or the air pressure indicative of the inhalation event 502b Receive, at the oxygen supply monitor, remote sensor data representing a physiological parameter of a patient to whom oxygen is being administered via the gas delivery system 504

Detect an alert condition based on the data generated by the oxygen supply monitor during the operation of the oxygen gas delivery system, and generate an alert in response to detecting the alert condition 506

Predict a prospective acute healthcare event based on the data generated by the oxygen supply monitor during the operation of the oxygen gas delivery system 508

FIG. 5

SYSTEM AND METHOD FOR POINT-OF-DELIVERY PATIENT OXYGEN SUPPLY MONITORING

CROSS-REFERENCE TO RELATED APPLICATIONS

This application is a bypass continuation of International Application No. PCT/US2023/062057, filed Feb. 6, 2023 and titled "SYSTEM AND METHOD FOR POINT-OF-DELIVERY PATIENT OXYGEN SUPPLY MONITOR-ING," which claims priority to and the benefit of U.S. Provisional Patent Application No. 63/312,490, filed Feb. 22, 2022 and titled "SYSTEM AND METHOD FOR POINT-OF-DELIVERY PATIENT OXYGEN SUPPLY MONITORING," the contents of each of which are incorporated by reference herein in their entireties.

FIELD

The present disclosure relates to systems and methods for monitoring patient health, and more specifically, for in-situ monitoring of oxygen therapy at the point of delivery.

BACKGROUND

Oxygen therapy, in medicine, is the administration of oxygen as a medical treatment, to patients with chronic illnesses such as hypoxemia, carbon monoxide toxicity, and cluster headache, as well as for other acute conditions in which tissues such as the brain and heart are at risk of oxygen deprivation. Stationary and portable oxygen storage systems can be designed for hospital or home use.

SUMMARY

In some embodiments, an apparatus for patient oxygen supply monitoring includes a housing, a microcontroller, at least one sensor, and a power supply. The housing has at least one port for mechanically coupling to a gas supply tube of an oxygen gas delivery system. The microcontroller is positioned within the housing, and the at least one sensor is operably coupled to the microcontroller and positioned within the housing. The power supply is positioned within the housing and configured to supply power, during opera-tion, to the microcontroller and to the at least one sensor. The microcontroller monitors the oxygen gas delivery system by receiving data generated by the at least one sensor when the at least one port is mechanically coupled to the gas supply tube and when oxygen is flowing through the at least one port.

In some embodiments, an apparatus includes a housing, an electronics assembly, and a power supply. The electronics assembly is disposed within the housing and including a processor, a memory, a transceiver, and at least one sensor. The power supply is configured to supply power to the electronics assembly. The housing is configured to attach to an oxygen gas delivery system such that, during a delivery of oxygen via the oxygen gas delivery system, a primary oxygen flow path is defined between an oxygen supply of the oxygen gas delivery system and an oxygen administration assembly of the oxygen gas delivery system, the primary oxygen flow path passing through a portion of the apparatus. The electronics assembly is configured to generate, based on data from the at least one sensor and during the delivery of the oxygen via the oxygen gas delivery system, at least one of oxygen flow data or inhalation data. The electronics assembly is also configured to cause transmission, via the transceiver, of the at least one of the oxygen flow data or the inhalation data to a remote compute device.

In some embodiments, an apparatus includes a housing, an electronics assembly, and a power supply. The electronics assembly is disposed within the housing and including a processor, a memory, a transceiver, and at least one sensor. The power supply is configured to supply power to the electronics assembly. The housing is configured to attach to an oxygen gas delivery system such that, during a delivery of oxygen via the oxygen gas delivery system, a primary oxygen flow path is defined between an oxygen supply of the oxygen gas delivery system and an oxygen administration assembly of the oxygen gas delivery system, a portion of the oxygen flows to the electronics assembly, and the primary oxygen flow path does not pass through a portion of the apparatus. The electronics assembly is configured to gener-ate, based on data from the at least one sensor and during the delivery of the oxygen via the oxygen gas delivery system, at least one of oxygen flow data or inhalation data. The electronics assembly is also configured to cause transmis-sion, via the transceiver, of the at least one of the oxygen flow data or the inhalation data to a remote compute device.

In some embodiments, a method for patient oxygen supply monitoring includes monitoring an operation of an oxygen gas delivery system by detecting, via an oxygen supply monitor coupled to the oxygen gas delivery system and during operation of the oxygen gas delivery system, at least one of an oxygen flow or an air pressure indicative of an inhalation event. The oxygen supply monitor is coupled to the oxygen gas delivery system in one of an in-line configuration or an offset configuration. The monitoring of the operation of the oxygen gas delivery system also includes at least one of storing or causing transmission of data generated by the oxygen supply monitor during the operation of the oxygen gas delivery system, based on the detecting of the at least one of the oxygen flow or the air pressure indicative of the inhalation event.

BRIEF DESCRIPTION OF THE DRAWINGS

FIG. 5 is a flow diagram showing a method of monitoring a patient oxygen supply using an oxygen supply monitor, according to some embodiments.

DETAILED DESCRIPTION

Figure 1A:
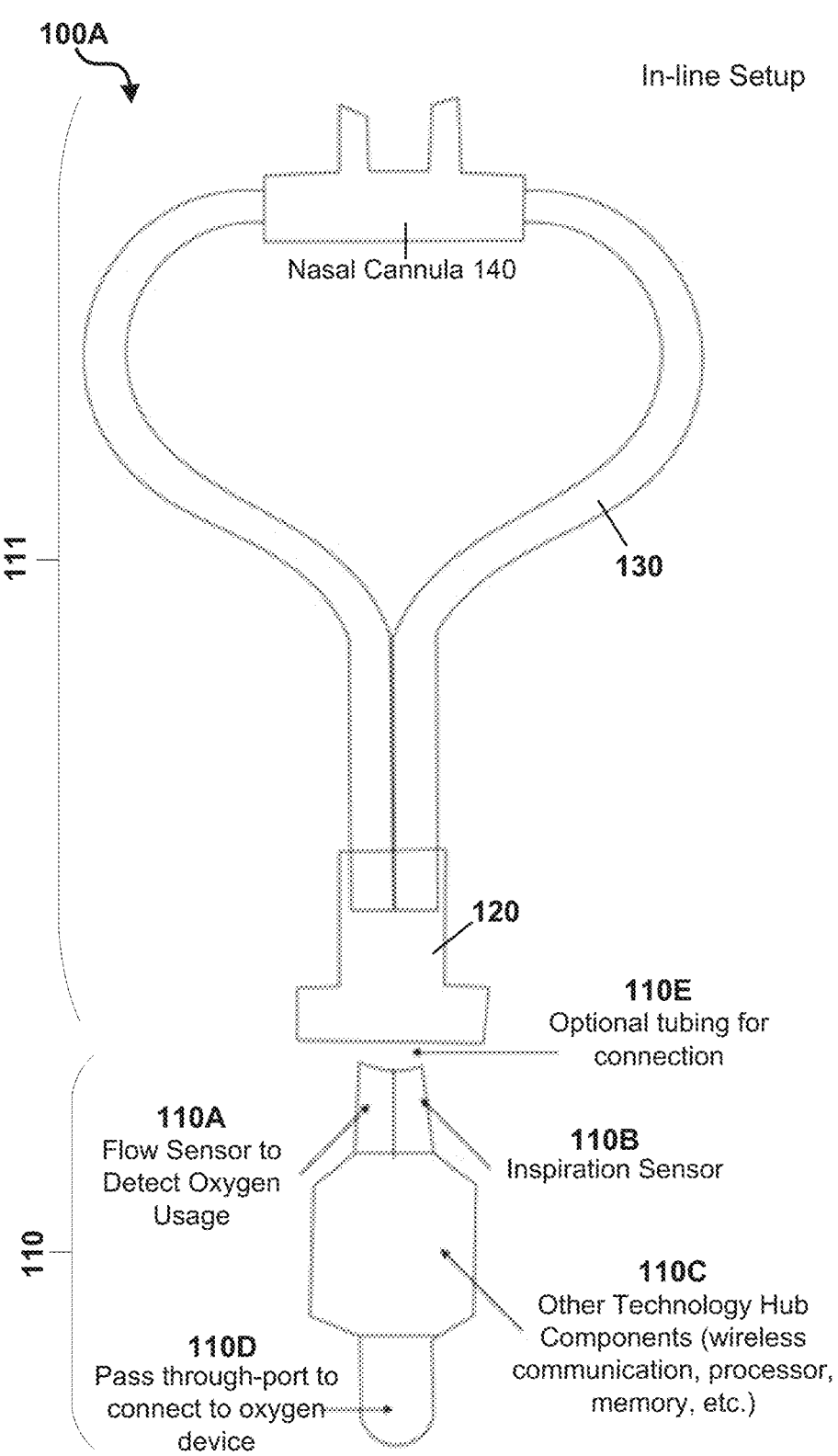
FIG. 1A shows a first implementation of an oxygen supply monitor, in an in-line configuration, according to some embodiments.

Patients with chronic respiratory diseases, such as inter-stitial lung disease (ILD) and chronic obstructive pulmonary disease (COPD), can experience exacerbations, or the acute worsening of respiratory symptoms without obvious clinical cause, which can be life-threatening. Acute exacerbations are strongly associated with a decrease in lung function as well as an increase in morbidity, hospital admissions, and health costs. Acute exacerbation of ILD are a dreaded occurrence with a grim prognosis: literature suggests that overall survival after hospital admission for an acute ILD exacerbation (AE-ILD) is very poor, with 67% at 1 month and 40% after 3 months, and overall mortality of AE-ILD ranging from 34-83%. The devastating nature of acute exacerbations supports the need for early detection and management of disease worsening to prevent irreversible lung damage. The American Thoracic Society Oxygen Working Group has identified a lack of evidence-based clinical practice guidelines for appropriate use of home oxygen as a critical gap in the care of patients. Thus, a need exists for improved remote patient monitoring (RPM) technologies to monitor and assess the ongoing respiratory needs of patients with chronic respiratory diseases.

Some known passive RPM technologies include patient wearables, e.g., sensor "tags" that can monitor physiological data such as respiratory effort, steps, and pulse. Other known RPM systems include patient-facing software applications ("apps") that communicate with multiple Bluetooth® sensors/devices such as actigraphy sensors, heart rate sensors, and pulse oximeters, and compile/present their data. Such known technologies, however, are not designed for use in conjunction with portable oxygen systems. In addition, some known manufacturers of portable oxygen concentrators (POC) have released oxygen systems with onboard sensors capable of relaying data back to a central dashboard and/or to patient applications. Such systems, however, are limited to device-specific analytics such as battery life, hours of use, and oxygen setting.

Embodiments of the present disclosure address the foregoing limitations by providing a compact, portable oxygen supply monitor that can be used passively on a variety of different oxygen equipment, to capture unique types of data specific to a patient's usage of oxygen, with minimal or no modification to the oxygen equipment, and without interfering with their workflow, equipment or bodily motion. Systems described herein can also function as a hub that can be paired with multiple biometric sensors on the patient's body. By passively monitoring oxygen delivery using systems and methods set forth herein, the process of communicating vital respiratory health signals from patients to physicians can be made faster, more efficient, more accurate, for a diverse set of medical oxygen supply sources. In addition, data collected with oxygen supply monitors of the present disclosure can be used for advanced analytical purposes such as detecting and predicting prospective acute healthcare events such as acute respiratory exacerbations. In some implementations, the detection and prediction of acute healthcare events is performed, at least in part, onboard the oxygen supply monitor, and associated detected/predicted healthcare data can be at least one of: displayed via a display of the oxygen supply monitor, or transmitted to at least one remote compute device. In other implementations, the detection and prediction of acute healthcare events is performed, at least in part, via at least one remote compute device operably coupled to, and in communication with, the oxygen supply monitor (e.g., via a wireless network communication channel), and associated detected/predicted healthcare data can be at least one of: displayed via a display of the at least one remote compute device, or transmitted from the at least one remote compute device to the oxygen supply monitor for display thereon.

In some embodiments, an oxygen supply monitor is configured to be removably attached to an oxygen gas delivery system. In other words, in some configurations, the oxygen supply monitor can be mechanically and/or fluidly coupled (e.g., via a cannula connector) and secured to a portion of the oxygen gas delivery system, and subsequently removed for servicing or replacement without damaging the oxygen gas delivery system. In some such implementations, the oxygen supply monitor includes at least two ports, where a first one of the ports is configured to connect to a first tubing portion and a second one of the ports is configured to connect to a second tubing portion of the oxygen gas delivery system. In other such implementations, the oxygen supply monitor includes at least one port and a single tube, such that a first tubing portion of the oxygen gas delivery system connects to a first port from the at least one port, and the tube connects (e.g., via a coupler or other mechanical attachment) to a second tubing portion of the oxygen gas delivery system. In still other such implementations, the oxygen supply monitor includes a pair of tubes, such that a first tubing portion of the oxygen gas delivery system connects (e.g., via a coupler or other mechanical attachment) to a first tube from the pair of tubes, and a second tubing portion of the oxygen gas delivery system connects (e.g., via a coupler or other mechanical attachment) to a second tube from the pair of tubes.

In some embodiments, an oxygen supply monitor includes a centralized hub unit, implemented in hardware and/or software, and configured to receive/store biometric information of a patient. The oxygen supply monitor can include, for example, a wireless communication module (e.g., a transceiver), a memory for data storage, and one or more sensors configured to detect inspiration and pressure within an oxygen flow path. In some implementations, the oxygen flow path passes through the oxygen supply monitor, while in other implementations, the oxygen flow path does not pass through the oxygen supply monitor but the oxygen supply monitor includes a recess or chamber that is in fluid communication with the oxygen flow path. Optionally, the oxygen supply monitor can be configured to pair with (i.e., wirelessly communicate with) one or more additional sensors or sensor systems that are not onboard the oxygen supply monitor. Such sensors or sensor systems can include (but are not limited to), any one or combination of: heart rate sensor(s), blood pressure sensor(s), oxygen saturation (SpO$_2$) sensor(s) (e.g., pulse oximeter(s)), actigraphy sensor (s), blood glucose sensor(s), biokinetic sensor(s), temperature sensor(s), humidity sensor(s), audio sensor(s), electrocardiogram(s), electroencephalogram(s), electromyography sensor(s), electrochemical sensor(s), impedance sensor(s), microelectromechanical (MEMS) sensor(s), etc. In some implementations, the sensors or sensor systems do not include a hot wire anemometer.

During use, in some implementations, the oxygen supply monitor is positioned between a gas spigot of an oxygen gas delivery system and a cannula of the oxygen gas delivery system. In other implementations, the oxygen supply monitor is attached to an outlet of a medical oxygen supply device such as an oxygen concentrator or an oxygen tank.

Although shown and described herein as applicable to oxygen gas delivery systems, oxygen supply monitor embodiments of the present disclosure can, alternatively or additionally, be used for other types of fluid delivery systems, such as nitrous oxide, nitrogen/oxygen mixtures, helium/oxygen mixtures, anesthetics, hypercarbic mixtures, hypoxic mixtures, carbon monoxide, and hydrogen sulfide.

In some embodiments, a patient oxygen monitoring system includes an oxygen supply monitor configured (e.g., dimensioned and/or shaped) to attach to an outlet of an oxygen supply device. Examples of suitable oxygen supply devices can include, but are not limited to: portable oxygen concentrator ("POC") systems such as continuous flow oxygen concentrators and pulse dose (or "intermittent flow") oxygen concentrators, ambulatory tanks, portable tanks, liquid oxygen systems, etc. The patient oxygen monitoring system also includes an oxygen administration device, such as a nasal cannula (see, e.g., FIGS. 4 and 6, discussed below), a face mask (see, e.g., FIG. 7, discussed below), or a transtracheal catheter. The oxygen supply monitor can include a controller (e.g., a microcontroller) configured to gather data about the oxygen that flows through the patient oxygen monitoring system, and optionally one or more sensors. The oxygen supply monitor can also include (e.g., within the controller) a memory to store data detected by the oxygen supply monitor and/or a transceiver configured to wirelessly transmit the data to a remote compute device (e.g., via a telecommunications network). An oxygen flow through the patient oxygen monitoring system may be predetermined and pre-set at the oxygen supply device and/or at the oxygen supply monitor, for example as prescribed by a physician (e.g., 1 liter per minute (LPM), 2 LPM, 3 LPM, 4 LPM, 5 LPM, 6 LPM, 7 LPM, 8 LPM, 9 LPM, 10 LPM, or between 1 LPM and 10 LPM). In some implementations, the patient oxygen monitoring system includes a humidifier and/or a heater to condition the oxygen prior to delivery at the patient, for example to prevent drying of the patient's airways.

In some embodiments, an oxygen supply monitor includes a controller and is secured to an oxygen supply outlet such that oxygen flowing from the oxygen supply outlet enters (e.g., via an input port) and passes through the oxygen supply monitor. The controller can be in wired or wireless communication with one or more sensors (including local sensors and/or remote sensors) that collect, or are indicative of, parameters associated with the oxygen supply gas flow and/or physiologic parameters associated with a patient/user. Such parameters can include, but are not limited to: pressure within the oxygen flow path, inhalation rate, blood pressure, heart rate, blood oxygen saturation, and pulse oximetry ($SpO_2$) data. The oxygen supply monitor also includes an outlet port for delivery of the oxygen flow originating from the oxygen supply device and passing through the oxygen supply monitor to oxygen tubing and a nasal cannula, oxygen mask, or similar oxygen delivery device. The remote sensors can include, for example, wearable sensors, Internet of Things (IoT) sensors, sensors embedded in other medical equipment, etc. In some implementations, the input port is on a first end of the oxygen supply monitor and the output port is on a second end of the oxygen supply monitor, the first end being opposite the second end. In other implementations, the input port is on a first end of the oxygen supply monitor and the output port is on a second end of the oxygen supply monitor, the first end being adjacent to (e.g., on a face that orthogonal to) the second end. In still other implementations, the input port and the output port of the oxygen supply monitor are positioned on a common side, face, or surface of the oxygen supply monitor.

The parameters associated with the oxygen supply gas flow and/or the physiologic parameters associated with the patient/user, whether generated locally at the oxygen supply monitor or received at the oxygen supply monitor from external sensors, can be stored by a microprocessor of the oxygen supply monitor and optionally one or more of: transmitted to one or more remote compute devices (e.g., for display thereon), analyzed as part of a remote patient monitoring process, or integrated into a report that is stored and/or transmitted by the oxygen supply monitor.

In some implementations, the controller is in wireless communication with one or more remote compute devices, such as a mobile compute device (e.g., a smartphone) and/or one or more servers. The controller may receive wireless signals from the one or more remote compute devices, for example representing one or more of: alerts, commands (e.g., to activate or deactivate the oxygen supply monitor or controller), analytics data, remote sensor data, patient data, etc. The wireless signals may be sent to the controller, for example, using a Greedy Perimeter Stateless Routing (GPSR) routing protocol.

In some implementations, the oxygen supply monitor can generate an alert based on the parameters associated with the oxygen supply gas flow and/or the physiologic parameters associated with the patient/user. Such alerts can be triggered by one or more individual values of such parameters, or by a trend detected over time in one or more of such parameters. Alerts can be implemented by one or more of: an audible sound emitted from the oxygen supply monitor itself (e.g., from a speaker onboard the oxygen supply monitor), illumination of an indicator of the oxygen supply monitor itself (e.g., a light-emitting diode ("LED") onboard the oxygen supply monitor), causing display of a text-based alert at the oxygen supply monitor itself (e.g., via a display onboard the oxygen supply monitor), or generating and transmitting a signal representing an alert to one or more remote compute devices (e.g., via wireless communication therewith).

In some implementations, at least one of the inlet port or the outlet port is a hose barb (i.e., a barbed hose fitting) for connection to plastic oxygen tubing.

In some implementations, at least one of the inlet port or the outlet port is a hose barb for plastic tubing having, for example, an inner diameter of about $\frac{3}{16}$".

In some implementations, at least one of the inlet port or the outlet port is configured to connect to a single lumen oxygen supply tube.

In some implementations, at least one of the inlet port or the outlet port is configured to connect to a dual lumen oxygen supply tube.

FIG. 1A shows a first implementation of an oxygen supply monitor system 100A, with an oxygen supply monitor in an in-line configuration ("in-line setup"), according to some embodiments. As shown in FIG. 1A, the oxygen supply monitor 110 includes a flow sensor 110A configured to detect oxygen usage of a patient over time, an inspiration sensor 110B (i.e., a sensor that can detect/measure pressure and/or flow changes, and correlate the pressure and/or flow change data to one or more inspiration profiles of a patient/user), a technology hub 110C (including electronics such as components for wireless communications, a processor, memory, etc.), and a pass-through port 110D for connection to an oxygen supply device (e.g., for connection to tubing, or to a regulator outlet, or to a humidifier outlet, or directly to an oxygen supply tank outlet, etc.). The oxygen supply monitor 110 optionally also includes, or is configured to couple/mate to, an additional segment of tubing 110E for securing a connection between the oxygen supply monitor 110 and an oxygen administration assembly 111 including a connector 120 (e.g., a wye connector or an end connector), gas supply tubing 130 (in this case, oxygen supply tubing), and a nasal cannula 140 including a pair of nasal prongs for delivery of oxygen to nostrils of a patient.

In some implementations, the technology hub 110C includes a display screen configured to display and/or an audio port configured to output alerts (e.g., user-customized alerts), real-time measurements, summary information, etc.

In some implementations, technology hub 110C is configured to receive wireless communications (e.g., via GPSR) directly from one or more sensors of oxygen supply monitor 110 and/or from one or more compute devices, without an intervening electronic device or compute device. Alternatively or in addition, the technology hub 110C and one or more of the flow sensor 110A, the inspiration sensor 110B, or the pass-through port 110D are co-located within a common/shared housing, to facilitate the prompt relaying (e.g., via video or text display and/or via an audio output) of information, alerts, and/or analysis directly to the patient/ wearer of the oxygen supply monitor system 100A.

Figure 1B:
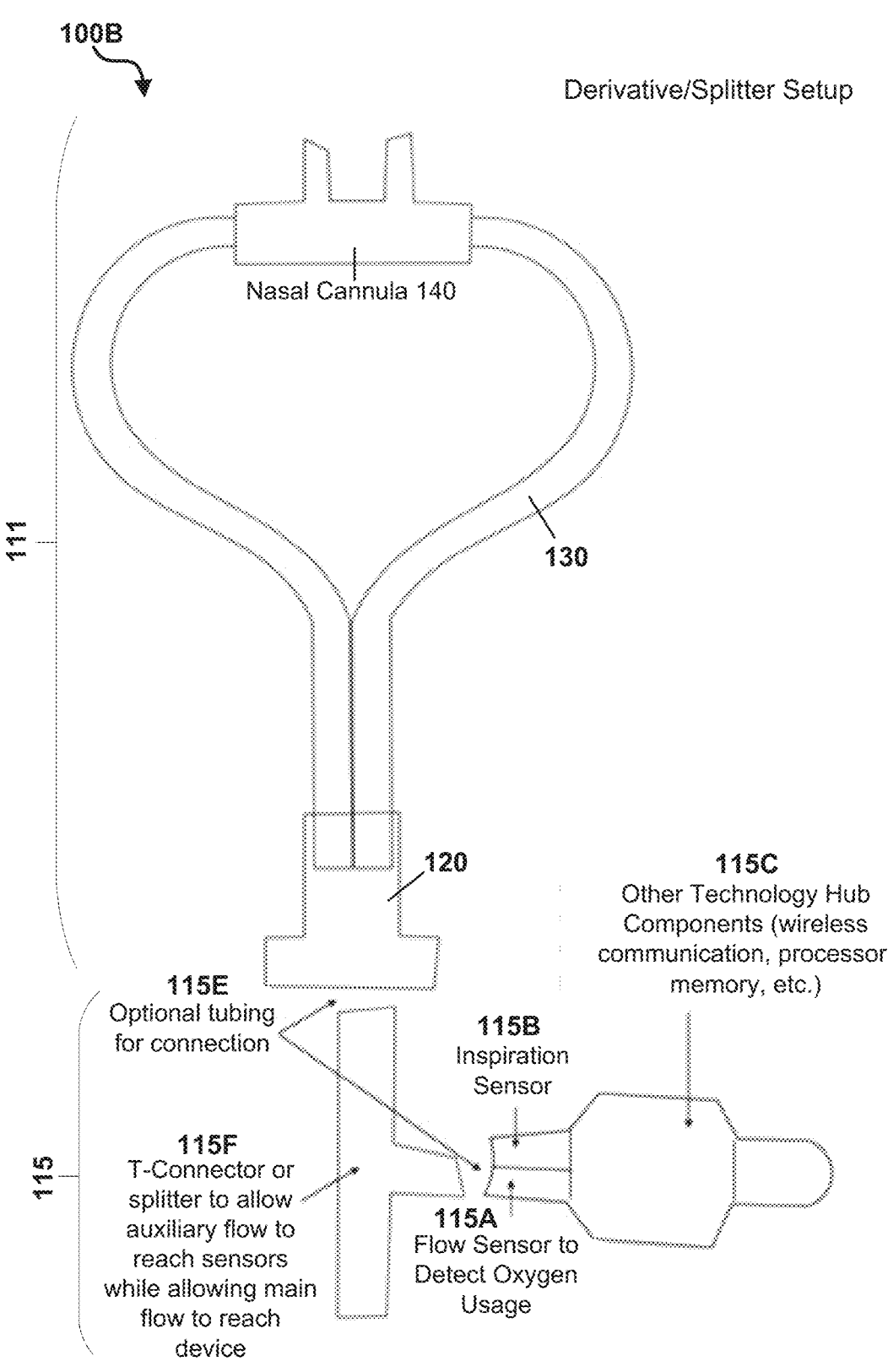
FIG. 1B shows a second implementation of an oxygen supply monitor, in an offset configuration, according to some embodiments.

FIG. 1B shows a second implementation of an oxygen supply monitor system 100B, with an oxygen supply monitor in an offset configuration ("splitter setup"), according to some embodiments. As shown in FIG. 1B, and similar to the oxygen supply monitor 110 of FIG. 1A, the oxygen supply monitor 115 includes a flow sensor 115A configured to detect oxygen usage of a patient over time, an inspiration sensor 115B (i.e., a sensor that can detect inhalation), and a technology hub 115C including electronics such as components for wireless communications, a processor, memory, etc.). The oxygen supply monitor 115 also includes a splitter or t-connector 115F configured to allow an auxiliary flow of oxygen to reach sensors of the technology hub 115C while also allowing a main/primary flow of oxygen to pass through to reach the oxygen administration assembly 111. The splitter or t-connector 115F is configured to connect to the technology hub 115C, an oxygen supply device (e.g., tubing, a regulator outlet, a gas port, a gas spigot, a humidifier outlet, or directly to an oxygen supply tank outlet, etc.), and the oxygen administration assembly 111. The oxygen supply monitor 115 optionally also includes, or is configured to couple/mate to, an additional segment of tubing 115E for securing a connection between the oxygen supply monitor 115 and the oxygen administration assembly 111. As in FIG. 1A, the oxygen administration assembly 111 includes a connector 120 (e.g., a wye connector or an end connector), gas supply tubing 130, and a nasal cannula 140 including a pair of nasal prongs for delivery of oxygen to nostrils of a patient. In the configuration of FIG. 1B, the oxygen administration assembly 111 can include a dual-lumen gas supply tubing 130. The dual-lumen gas supply tubing 130 can include a breathing lumen and an inspiration lumen. A pressure sensor of the technology hub 115C may be positioned such that it can detect the oxygen flow travelling through the breathing lumen, while an inspiration sensor of the technology hub 115C may be positioned such that it can detect inspiration in the other lumen.

Although the splitter or t-connector 115F is shown and described with reference to FIG. 1B as being implemented as a t-shaped connector, in other implementations, the splitter or t-connector 115F can have one or more of the following configurations: (1) a connector having (a) a primary flow path defined therein (i.e., to extend from an oxygen supply to the oxygen administration assembly 111), e.g., a length of tube, and having a first inner diameter, and (b) a secondary flow path defined therein (i.e., to extend from primary flow path to the technology hub 115C), e.g., a length of tube, and having a second inner diameter less than the first inner diameter; or (2) a multi-lumen connector comprising tubing, where the multi-lumen is either concentric or side-by-side.

In some implementations, the technology hub 115C includes a display screen configured to display and/or an audio port configured to output alerts (e.g., user-customized alerts), real-time measurements, summary information, etc.

In some implementations, technology hub 115C is configured to receive wireless communications (e.g., via GPSR) directly from one or more sensors of oxygen supply monitor 115 and/or from one or more compute devices, without an intervening electronic device or compute device. Alternatively or in addition, the technology hub 115C and one or more of the flow sensor 115A, the inspiration sensor 115B, the pass-through port 115D, or the t-connector 115F are co-located within a common/shared housing, to facilitate the prompt relaying (e.g., via video or text display and/or via an audio output) of information, alerts, and/or analysis directly to the patient/wearer of the oxygen supply monitor system 100B.

Figure 2:
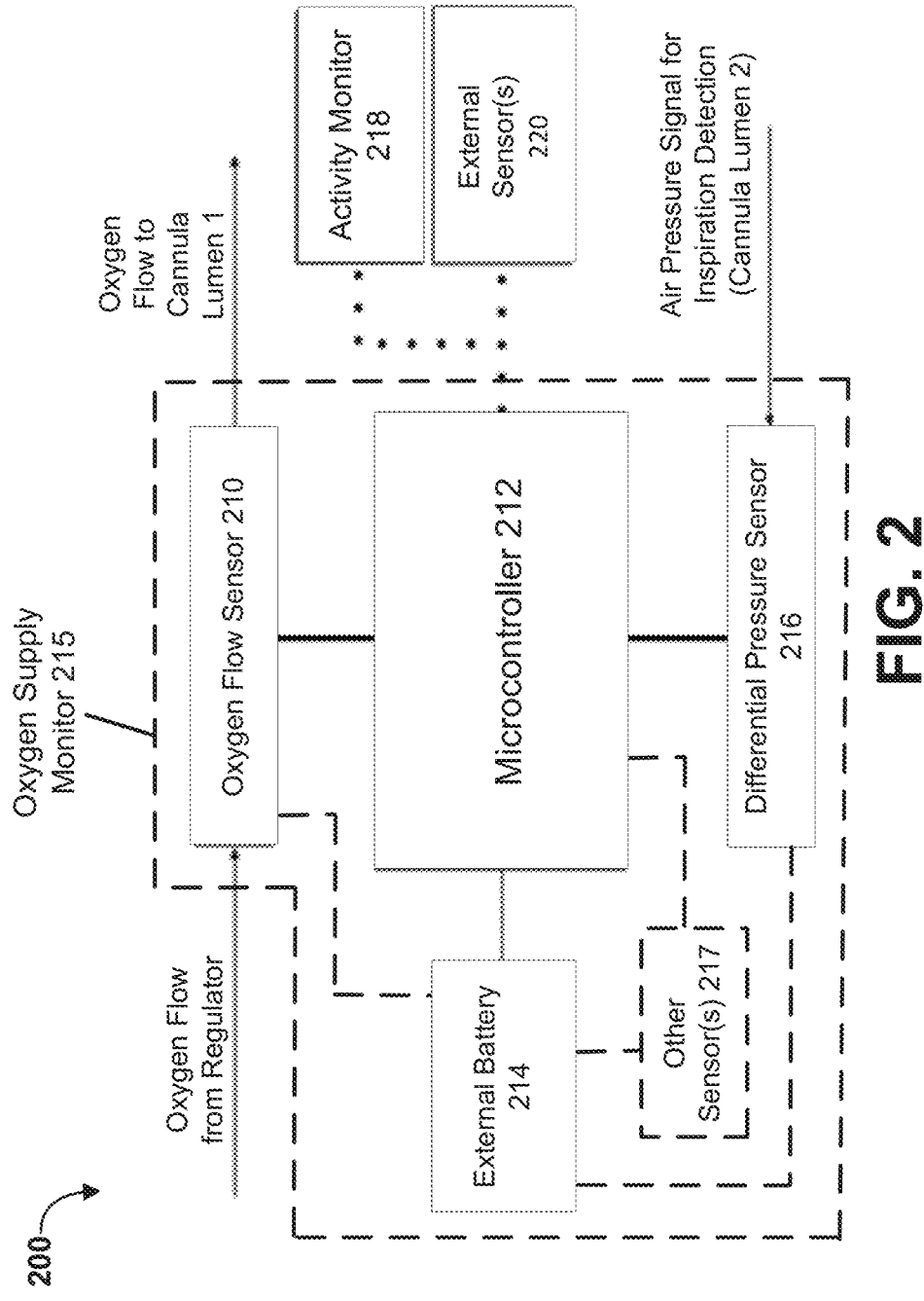
FIG. 2 is a system diagram showing an example imple-mentation of an oxygen supply monitor, according to some embodiments.

FIG. 2 is a system diagram showing an example implementation of an oxygen supply monitor, according to some embodiments. As shown in FIG. 2, a system 200 includes an oxygen supply monitor 215, and the oxygen supply monitor 215 can include one or more of an oxygen flow sensor 210, a microcontroller 212, a power supply (e.g., a battery) 214, a differential pressure sensor 216, and optionally one or more additional sensors 217 (e.g., temperature sensor(s), gas purity sensor(s)/analyzer(s) (e.g., oxygen purity sensor(s)/ analyzer(s)), and/or humidity sensor(s)). The power supply 214 can supply power to the microcontroller 212 and, optionally, one or each of the oxygen flow sensor 210, the differential pressure sensor 216, and the one or more additional sensors 217. All of the foregoing components, or any subset thereof, may be co-located within a common housing. The oxygen flow sensor 210 can be "in-line" such that an oxygen flow is received at the oxygen flow sensor 210 from a regulator of an oxygen supply (either directly or via one or more intermediate components, such as a humidifier), and such that oxygen flow passes through the oxygen flow sensor 210 and is delivered to a first lumen of a cannula for delivery to a patient. The differential pressure sensor 216 can receive an air pressure signal via a second lumen of the cannula, for detection of inspiration/inhalation by the patient. The microcontroller 212 can optionally be configured to receive sensor data from one or more external sensors 220 (e.g., via wireless network communication). Alternatively or in addition, the microcontroller 212 can be configured to transmit data detected/received/stored by the microcontroller 212 to an activity monitor 218 (e.g., via wireless network communication). The activity monitor 218 can be implemented as a remote compute device, such as a mobile compute device, for example so that data generated by the microcontroller 212 can be displayed via a graphical user interface (GUI) of the remote compute device. Components of the system of FIG. 2 (or portions thereof) can be configured to function within various types of network environments that can include one or more devices and/or one or more server devices. For example, as used herein, a wireless telecommunications network (e.g., the wireless telecommunications network N of FIG. 3 can be, or can include, a local area network (LAN), a wide area network (WAN), and/or so forth. The network can be, or can include, a wireless network and/or wireless network implemented using, for example, gateway devices, bridges, switches, and/or so forth. The network can include one or more segments and/or can have portions based on various protocols such as Internet Protocol (IP) and/or a proprietary protocol. The network can include at least a portion of the Internet.

Figure 3:
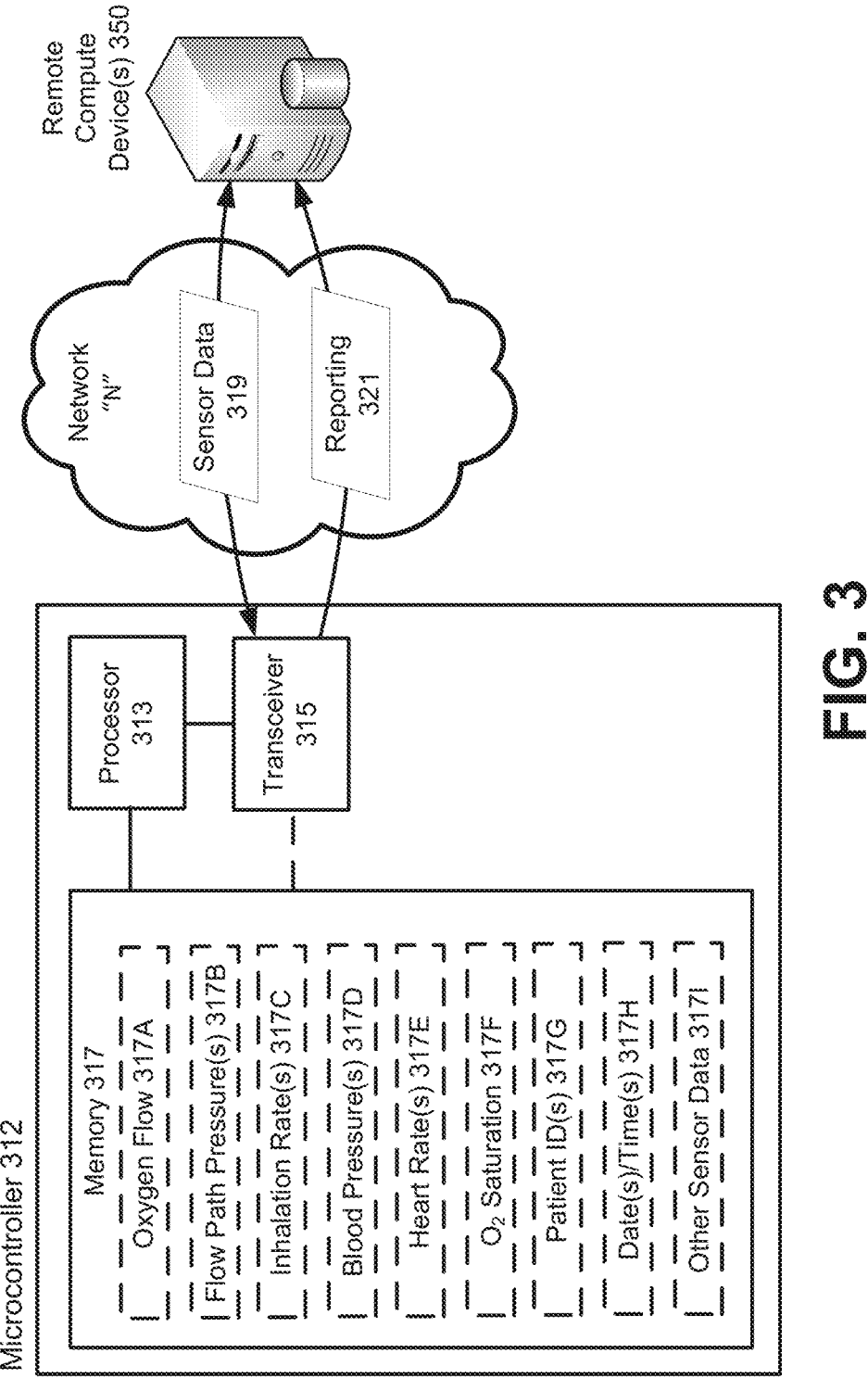
FIG. 3 shows an example microcontroller, compatible with the system of FIG. 2, according to some embodiments.

FIG. 3 shows an example microcontroller, compatible with the system 200 of FIG. 2 (i.e., suitable for use as the microcontroller 212 of FIG. 2), according to some embodiments. As shown in FIG. 3, the microcontroller 312 includes a processor 313 operably coupled to a transceiver 315 and a memory 317. Optionally, the transceiver 315 is also operably coupled to the memory 317. The memory 317 stores one or more of: oxygen flow data 317A, flow path pressure (s) 317B, inhalation/inspiration rate(s) 317C, blood pressure (s) 317D, heart rate(s) 317E, oxygen saturation data 317F, patent identifier(s) (IDs) 317G, dates and/or times 317H, and other sensor data 317I. The other sensor data 317I can include data generated by one or more sensors of an oxygen supply monitor within which the microcontroller 312 is positioned, and/or sensor data 319 received from one or more remote compute device(s) 350 via a wireless telecommunications network "N," the details of which may be as described above. The microcontroller 312 can also send sensor data 319 and/or reporting 321 to the one or more remote compute device(s) 350 via the wireless telecommunications network N. The reporting can include, for example, monitored patient-specific data collected, by the microcontroller, over time and during use by the patient of an oxygen supply device.

Figure 4:
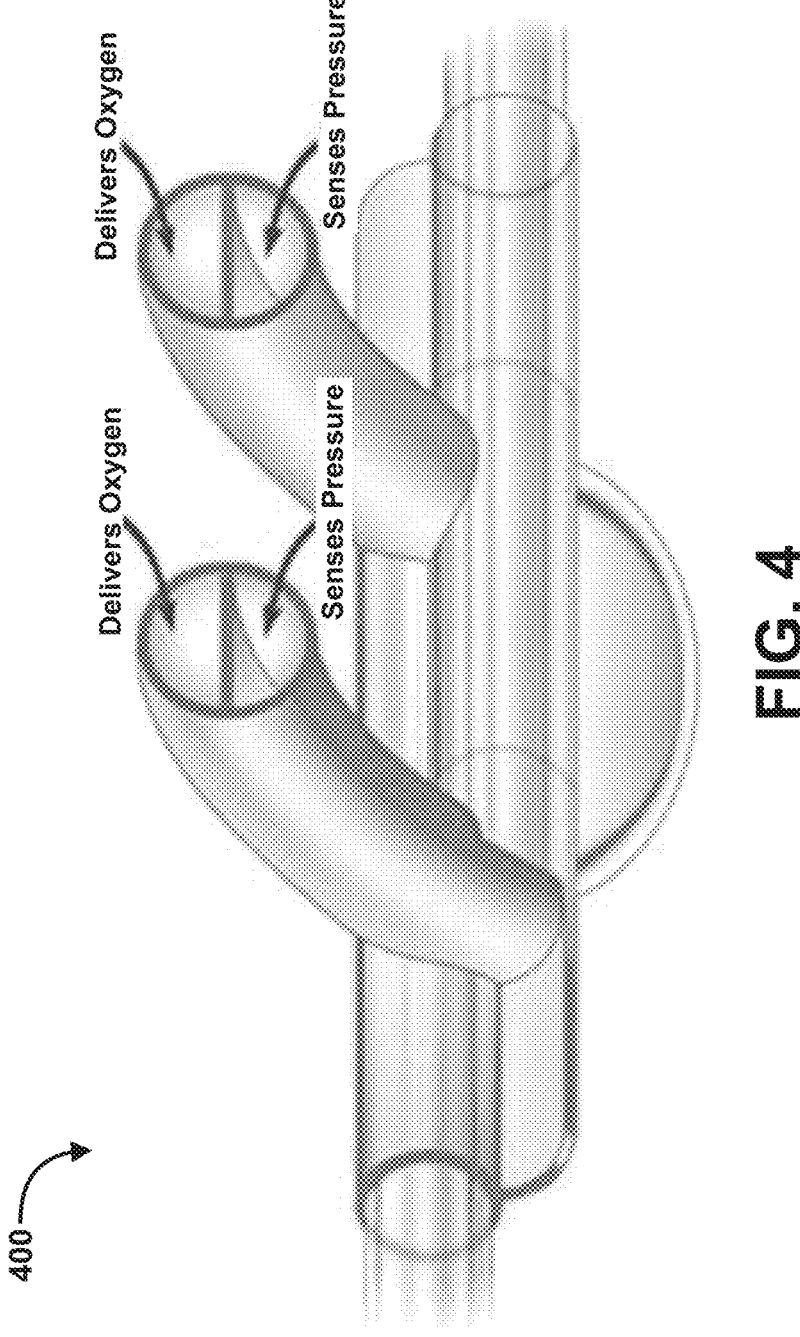
FIG. 4 is a diagram of a dual lumen cannula, according to some embodiments.

FIG. 4 is a diagram of a dual lumen cannula, according to some embodiments. As shown in FIG. 4, the dual lumen cannula 400 includes a pair of nasal prongs each having an associated breathing lumen for the delivery of oxygen to an associated nostril of the patient, and an associated inspiration lumen for the detection of inhalation/inspiration pressure associated with that nostril of the patient.

In some embodiments, an apparatus for patient oxygen supply monitoring includes a housing, a microcontroller, at least one sensor, and a power supply. The housing has at least one port for mechanically coupling to a gas supply tube of an oxygen gas delivery system. The microcontroller is positioned within the housing, and the at least one sensor is-operably coupled to the microcontroller and positioned within the housing. The power supply is positioned within the housing and configured to supply power, during operation, to the microcontroller and to the at least one sensor. The microcontroller monitors the oxygen gas delivery system by receiving data generated by the at least one sensor when the at least one port is mechanically coupled to the gas supply tube and when oxygen is flowing through the at least one port.

In some implementations, the at least one port includes a hose barb.

In some implementations, the at least one sensor includes at least two sensors, and the gas supply tube is a dual lumen gas supply tube. A first sensor from the at least two sensors is positioned to align with a first lumen of the dual lumen gas supply tube when the at least one port is mechanically coupled to the dual lumen gas supply tube, and a second sensor from the at least two sensors is positioned to align with a second lumen of the dual lumen gas supply tube when the at least one port is mechanically coupled to the dual lumen gas supply tube.

In some implementations, the at least one sensor includes an oxygen flow sensor.

In some implementations, the at least one sensor includes a differential pressure sensor.

In some implementations, the at least one sensor includes an oxygen flow sensor and a differential pressure sensor.

In some implementations, the at least one sensor includes an oxygen flow sensor, and the oxygen flows through the oxygen flow sensor when the at least one port is mechanically coupled to the gas supply tube and when the oxygen is flowing through the at least one port.

In some implementations, the at least one port includes at least two ports, and a second port from the at least two ports is configured to mechanically couple to an oxygen administration assembly. The oxygen administration assembly can include one of a nasal cannula, a face mask, or a transtracheal catheter.

In some embodiments, an apparatus includes a housing, an electronics assembly, and a power supply. The electronics assembly is disposed within the housing and including a processor, a memory, a transceiver, and at least one sensor. The power supply is configured to supply power to the electronics assembly. The housing is configured to attach to an oxygen gas delivery system such that, during a delivery of oxygen via the oxygen gas delivery system, a primary oxygen flow path is defined between an oxygen supply of the oxygen gas delivery system and an oxygen administration assembly of the oxygen gas delivery system, the primary oxygen flow path passing through a portion of the apparatus. The electronics assembly is configured to generate, based on data from the at least one sensor and during the delivery of the oxygen via the oxygen gas delivery system, at least one of oxygen flow data or inhalation data. The electronics assembly is also configured to cause transmission, via the transceiver, of the at least one of the oxygen flow data or the inhalation data to a remote compute device.

In some embodiments, an apparatus includes a housing, an electronics assembly, and a power supply. The electronics assembly is disposed within the housing and including a processor, a memory, a transceiver, and at least one sensor. The power supply is configured to supply power to the electronics assembly. The housing is configured to attach to an oxygen gas delivery system such that, during a delivery of oxygen via the oxygen gas delivery system, a primary oxygen flow path is defined between an oxygen supply of the oxygen gas delivery system and an oxygen administration assembly of the oxygen gas delivery system, a portion of the oxygen flows to the electronics assembly, and the primary oxygen flow path does not pass through a portion of the apparatus. The electronics assembly is configured to generate, based on data from the at least one sensor and during the delivery of the oxygen via the oxygen gas delivery system, at least one of oxygen flow data or inhalation data. The electronics assembly is also configured to cause transmission, via the transceiver, of the at least one of the oxygen flow data or the inhalation data to a remote compute device.

FIG. 5 is a flow diagram showing a method of monitoring a patient oxygen supply using an oxygen supply monitor, according to some embodiments. As shown in FIG. 5, the method 500 includes monitoring an operation of an oxygen gas delivery system, at 502, by detecting, at 502a, via an oxygen supply monitor coupled to the oxygen gas delivery system and during operation of the oxygen gas delivery system, at least one of an oxygen flow or an air pressure indicative of an inhalation event. The oxygen supply monitor is coupled to the oxygen gas delivery system in one of an in-line configuration or an offset configuration. The monitoring of the operation of the oxygen gas delivery system 502 also includes, at 502b, at least one of storing or causing transmission of data generated by the oxygen supply monitor during the operation of the oxygen gas delivery system, based on the detecting of the at least one of the oxygen flow or the air pressure indicative of the inhalation event. In some implementations, the method 500 also includes receiving, at 504, at the oxygen supply monitor, remote sensor data representing a physiological parameter of a patient to whom oxygen is being administered via the gas delivery system. In some implementations, the method 500 also includes detecting an alert condition, at 506, based on the data generated by the oxygen supply monitor during the operation of the oxygen gas delivery system, and generating an alert in response to detecting the alert condition. In some implementations, the method 500 also includes predicting a prospective acute healthcare event, at 508, based on the data generated by the oxygen supply monitor during the operation of the oxygen gas delivery system.

In some implementations, the oxygen supply monitor is coupled to the oxygen gas delivery system via two ports of the oxygen supply monitor, a first port from the two ports being coupled to a first segment of gas supply tube of the oxygen gas delivery system, and a second port from the two ports being coupled to a second segment of gas supply tube of the oxygen gas delivery system. At least one of the first segment of gas supply tube or the second segment of gas supply tube can be a dual lumen gas supply tube. The second segment of gas supply tube can be part of an oxygen administration assembly including one of a nasal cannula, a face mask, or a transtracheal catheter.

In some implementations, the oxygen supply monitor is coupled to the oxygen gas delivery system via at least one barbed hose fitting.

In some implementations, the oxygen supply monitor is coupled to the oxygen gas delivery system in the offset configuration and via a splitter.

Figure 6:
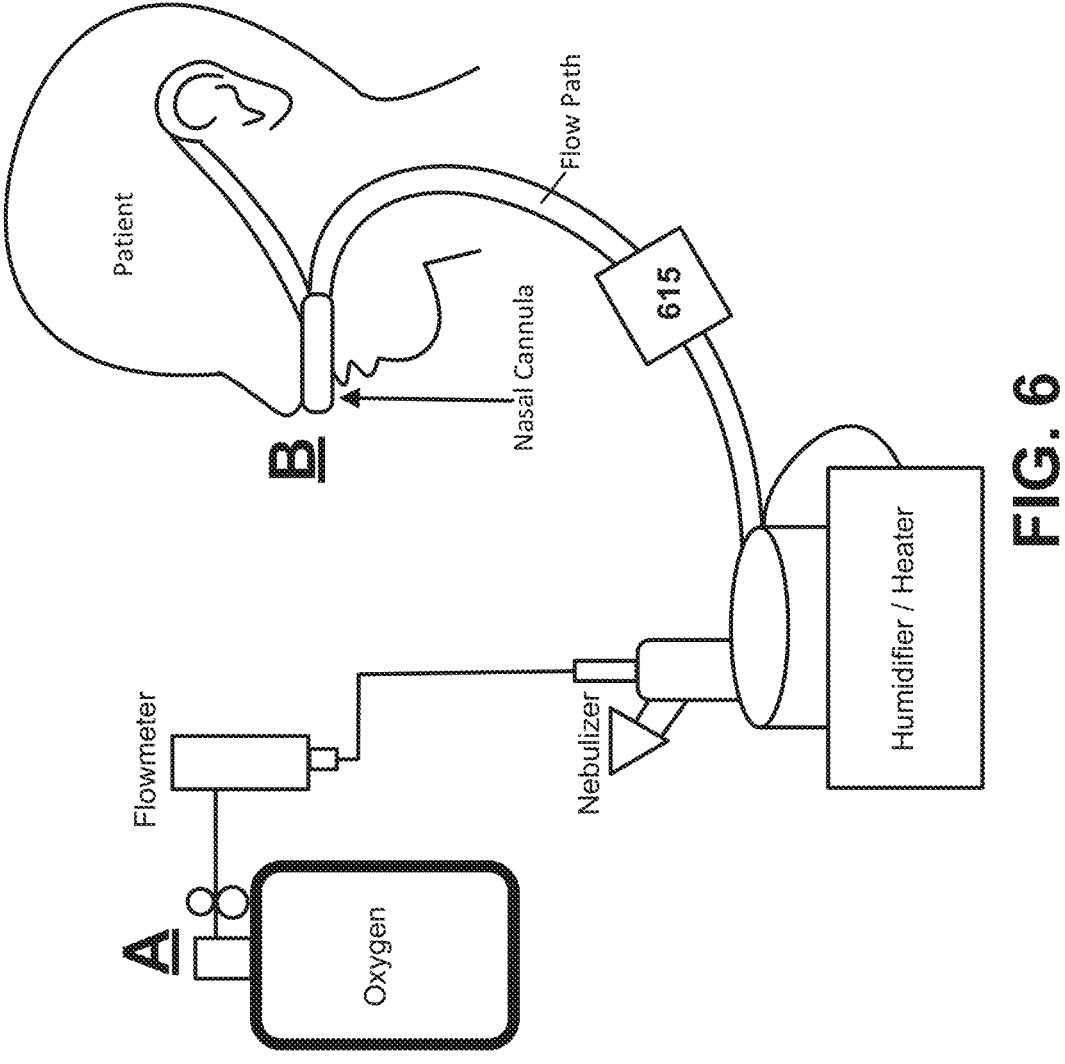
FIG. 6 shows an example oxygen supply monitor in a cannula-based application, according to some embodiments.

FIG. 6 shows an example oxygen supply monitor in a cannula-based application, according to some embodiments. As shown in FIG. 6, an oxygen delivery circuit or pathway extends from an oxygen tank/supply/source (at point "A"), optionally through one or more of a valve, a flowmeter, a nebulizer, a humidifier/heater, a flow path, and a nasal cannula (ending at the point of delivery of the oxygen to the patient, labelled as "B"). As also shown in FIG. 6, an oxygen supply monitor 615 is positioned in-line with the flow path of oxygen between the humidifier/heater and the nasal cannula. Although shown and described as being positioned between the humidifier/heater and the nasal cannula, in other implementations, the oxygen supply monitor 615 can be positioned at any location along the oxygen delivery circuit extending from A to B, and can have an "in-line" configuration, as discussed herein (i.e., connected to the overall oxygen delivery system in such a manner that the oxygen being supplied passes directly through the oxygen supply monitor 615 on its way to being delivered to the patient via the nasal cannula), or can have a splitter or offset configuration (e.g., connected to one or more components along the flow path in such a way that the oxygen being supplied does not pass directly through the oxygen supply monitor on its way to being delivered to the patient via the nasal cannula).

Figure 7:
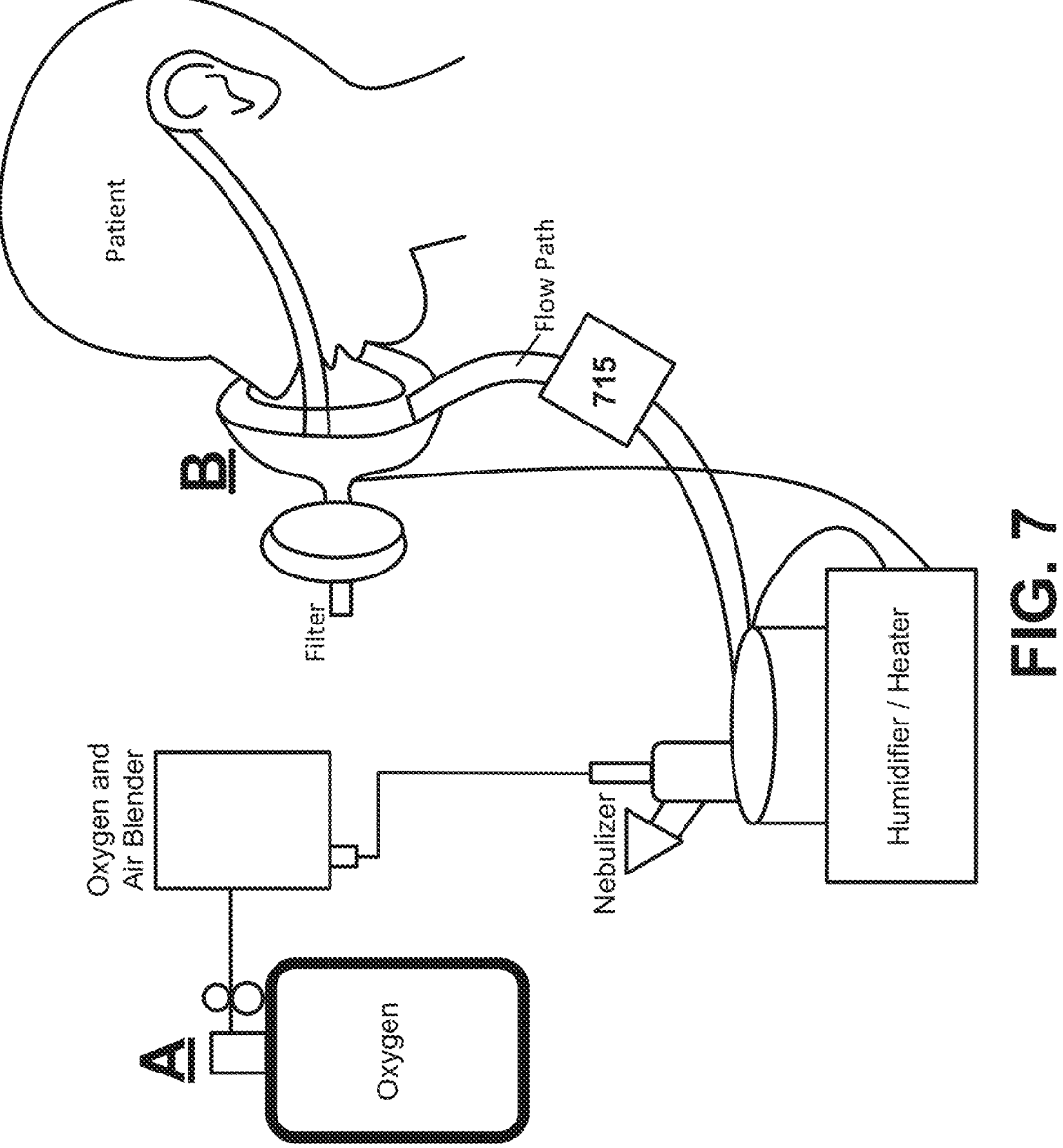
FIG. 7 shows an example oxygen supply monitor in a mask-based application, according to some embodiments.

FIG. 7 shows an example oxygen supply monitor in a mask-based application, according to some embodiments. As shown in FIG. 7, similar to the system of FIG. 6, an oxygen delivery circuit or pathway extends from an oxygen tank/supply/source (at point "A"), optionally through one or more of a valve, an oxygen and air blender, a nebulizer, a humidifier/heater, a flow path, and a face mask (ending at the point of delivery of the oxygen to the patient, labelled as "B"). As also shown in FIG. 6, an oxygen supply monitor 615 is positioned in-line with the flow path of oxygen between the humidifier/heater and the nasal cannula. Although shown and described as being positioned between the humidifier/heater and the nasal cannula, in other implementations, the oxygen supply monitor 615 can be positioned at any location along the oxygen delivery circuit extending from A to B, and can have an "in-line" configuration, as discussed herein (i.e., connected to the overall oxygen delivery system in such a manner that the oxygen being supplied passes directly through the oxygen supply monitor 615 on its way to being delivered to the patient via the face mask), or can have a splitter or offset configuration (e.g., connected to one or more components along the flow path in such a way that the oxygen being supplied does not pass directly through the oxygen supply monitor on its way to being delivered to the patient via the face mask).

As discussed above, in some embodiments, an oxygen supply monitor can be implemented as an attachment to gas supply tubing, in either an in-line configuration or in an offset configuration. In in-line configurations, the oxygen supply monitor is interposed between, and operably coupled to, two distinct portions of an oxygen supply circuit, such that during use/operation, oxygen flow is received at the oxygen supply monitor from an oxygen supply (e.g., from a regulator thereof) of an oxygen gas delivery system, and oxygen flow passes through at least a portion of the oxygen supply monitor (e.g., via an oxygen flow sensor) and is delivered to an oxygen administration assembly (e.g., to a first lumen of a cannula) for delivery of the oxygen to a patient. In offset configurations, the oxygen supply monitor is positioned adjacent to a primary oxygen flow path such that, during use/operation, while the oxygen does not pass directly through the oxygen supply monitor on its way to being delivered to the patient via the nasal cannula, an auxiliary flow of oxygen reaches one or more sensors of the oxygen supply monitor.

In other embodiments, rather than being implemented as an attachment to gas supply tubing, an oxygen supply monitor can be implemented as an internal component of a portable or stationary oxygen concentrator. In some such implementations, the sensor(s) of the oxygen supply monitor can be in-line with a gas port/spigot of the oxygen concentrator, or can be in-line with (or offset from) an alternative lumen line before or after the gas port/spigot. Alternatively or in addition, an oxygen supply monitor can be implemented as part of a regulator of a tank-based oxygen gas delivery system, whereby the regulator itself includes a wireless capability (i.e., a transceiver) and one or more of the sensors described herein (i.e., any or all of the functionality shown and discussed with reference to FIG. 2). The regulator of the tank-based oxygen gas delivery system can be positioned between (and connected to each of) the oxygen tank and the gas port/spigot. Alternatively or in addition, an oxygen supply monitor can be directly integrated into a cannula of an oxygen administration assembly, for example with the one or more sensors of the oxygen supply monitor positioned to detect data/properties within the lumen of the oxygen administration assembly (e.g., similar to the oxygen administration assembly 111 of FIGS. 1A and 1B).

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The drawings are primarily for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

The entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

As used herein, the term "substantially" has a meaning similar to "mostly" or "to a great extent." For example, the phrase "a substantially uniform thickness" refers to a thickness value plus or minus a range of 10%.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The term "processor" should be interpreted broadly to encompass a general purpose processor, a central processing unit (CPU), a microprocessor, a digital signal processor (DSP), a controller, a microcontroller, a state machine and so forth. Under some circumstances, a "processor" may refer to an application specific integrated circuit (ASIC), a programmable logic device (PLD), a field programmable gate array (FPGA), etc. The term "processor" may refer to a combination of processing devices, e.g., a combination of a DSP and a microprocessor, a plurality of microprocessors, one or more microprocessors in conjunction with a DSP core or any other such configuration.

The term "memory" should be interpreted broadly to encompass any electronic component capable of storing electronic information. The term memory may refer to various types of processor-readable media such as random access memory (RAM), read-only memory (ROM), non-volatile random access memory (NVRAM), programmable read-only memory (PROM), erasable programmable read only memory (EPROM), electrically erasable PROM (EE-PROM), flash memory, magnetic or optical data storage, registers, etc. Memory is said to be in electronic communication with a processor if the processor can read information from and/or write information to the memory. Memory that is integral to a processor is in electronic communication with the processor.

The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may comprise a single computer-readable statement or many computer-readable statements.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately" when preceding a numerical value indicates the value plus or minus a range of 10%. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
a housing having at least one port defined therein, a first port from the at least one port configured to mechanically couple to a dual lumen gas supply tube of an oxygen gas delivery system;
a microcontroller disposed within the housing;
a first sensor operably coupled to the microcontroller and disposed within the housing, the first sensor aligned with a first lumen of the dual lumen gas supply tube when the at least one port is mechanically coupled to the dual lumen gas supply tube;
a second sensor different from the first sensor and operably coupled to the microcontroller and disposed within the housing, the second sensor aligned with a second lumen of the dual lumen gas supply tube and not the first lumen when the at least one port is mechanically coupled to the dual lumen gas supply tube; and
a power supply disposed within the housing and configured to supply power, during operation, to the microcontroller, the first sensor, and the second sensor,
the microcontroller configured to perform monitoring of the oxygen gas delivery system, the monitoring including receiving data generated by at least one of the first sensor or the second sensor when the at least one port is mechanically coupled to the dual lumen gas supply tube and when oxygen is flowing through the at least one port.

2. The apparatus of claim 1, wherein the at least one port includes a hose barb.

3. The apparatus of claim 1, wherein at least one of the first sensor or the second sensor includes an oxygen flow sensor.

4. The apparatus of claim 1, wherein at least one of the first sensor or the second sensor includes a differential pressure sensor.

5. The apparatus of claim 1, wherein the first sensor includes an oxygen flow sensor and the second sensor includes a differential pressure sensor.

6. The apparatus of claim 1, wherein:
at least one of the first sensor or the second sensor includes an oxygen flow sensor, and
the oxygen flows through the oxygen flow sensor when the at least one port is mechanically coupled to the dual lumen gas supply tube and when the oxygen is flowing through the at least one port.

7. The apparatus of claim 1, wherein the at least one port includes a second port configured to mechanically couple to an oxygen administration assembly.

8. The apparatus of claim 7, wherein the oxygen administration assembly includes one of a nasal cannula, a face mask, or a transtracheal catheter.

9. A method, comprising:
monitoring an operation of an oxygen gas delivery system by:
detecting, via an oxygen supply monitor coupled via a t-connector to the oxygen gas delivery system and during operation of the oxygen gas delivery system, at least one of an oxygen flow or an air pressure indicative of an inhalation event, the oxygen supply monitor being coupled to the oxygen gas delivery system in one of an in-line configuration or an offset configuration; and
at least one of storing or causing transmission of data generated by the oxygen supply monitor during the operation of the oxygen gas delivery system, based on the detecting of the at least one of the oxygen flow or the air pressure indicative of the inhalation event,
the oxygen gas delivery system including a dual lumen cannula, and
the oxygen supply monitor including a first sensor operably coupled to a microcontroller and aligned with a first lumen of the dual lumen cannula, and a second sensor different from the first sensor and operably coupled to the microcontroller, the second sensor aligned with a second lumen of the dual lumen cannula.

10. The method of claim 9, wherein the oxygen supply monitor is coupled to the oxygen gas delivery system via at least one barbed hose fitting.

11. The method of claim 9, further comprising receiving, at the oxygen supply monitor, remote sensor data representing a physiological parameter of a patient to whom oxygen is being administered via the gas delivery system.

12. The method of claim 9, further comprising:
detecting an alert condition based on the data generated by the oxygen supply monitor during the operation of the oxygen gas delivery system, and
generating an alert in response to detecting the alert condition.

13. The method of claim 9, further comprising predicting a prospective acute healthcare event based on the data generated by the oxygen supply monitor during the operation of the oxygen gas delivery system.

14. The method of claim 9, wherein the oxygen supply monitor is coupled to the oxygen gas delivery system in the offset configuration and via a splitter.

15. The apparatus of claim 1, wherein the microcontroller is further configured to predict a prospective acute healthcare event based on the data generated by the at least one of the first sensor or the second sensor during the operation of the oxygen gas delivery system.

* * * * *